United States Patent
Ying et al.

(10) Patent No.: US 11,118,171 B2
(45) Date of Patent: Sep. 14, 2021

(54) RECOMBINANT CORYNEBACTERIUM GLUTAMICUM FOR PRODUCING LYSINE BY BIOFILM CONTINUOUS FERMENTATION AND CONSTRUCTION METHOD THEREOF

(71) Applicant: Nanjing Tech University, Jiangsu (CN)

(72) Inventors: Hanjie Ying, Jiangsu (CN); Dong Liu, Jiangsu (CN); Yong Chen, Jiangsu (CN); Qingguo Liu, Jiangsu (CN); Pingkai Ouyang, Jiangsu (CN); Ming Lei, Jiangsu (CN); Huanqing Niu, Jiangsu (CN); Bin Yu, Jiangsu (CN); Di Zhang, Jiangsu (CN); Yuhan Yang, Jiangsu (CN); Shishi Wu, Jiangsu (CN)

(73) Assignee: Nanjing Tech University, Jiangsu (CN)

( * ) Notice: Subject to any disclaimer, the term of this patent is extended or adjusted under 35 U.S.C. 154(b) by 0 days.

(21) Appl. No.: 17/117,870

(22) Filed: Dec. 10, 2020

(65) Prior Publication Data
US 2021/0155917 A1 May 27, 2021

(30) Foreign Application Priority Data

Dec. 25, 2019 (CN) .......................... 201911354539.6

(51) Int. Cl.
| | |
|---|---|
| *C12N 9/52* | (2006.01) |
| *C12N 1/20* | (2006.01) |
| *C12N 15/52* | (2006.01) |
| *C12N 15/77* | (2006.01) |
| *C12P 13/08* | (2006.01) |
| *C12R 1/15* | (2006.01) |

(52) U.S. Cl.
CPC ................. *C12N 9/52* (2013.01); *C12N 1/20* (2013.01); *C12N 1/205* (2021.05); *C12N 15/52* (2013.01); *C12N 15/77* (2013.01); *C12P 13/08* (2013.01); *C12Y 304/24* (2013.01); *C12R 2001/15* (2021.05)

(58) Field of Classification Search
CPC .......... C12N 9/52; C12N 15/77; C12N 15/52; C12N 1/20; C12Y 304/24; C12P 13/08; C12R 1/15
See application file for complete search history.

(56) References Cited

U.S. PATENT DOCUMENTS

| | | | | |
|---|---|---|---|---|
| 6,822,084 B1 * | 11/2004 | Pompejus | .............. | C07K 14/34 435/252.3 |
| 7,332,310 B2 * | 2/2008 | Nakagawa | ............. | C07K 14/34 435/115 |
| 7,851,198 B2 * | 12/2010 | Park | ....................... | C07K 14/34 435/252.32 |

OTHER PUBLICATIONS

Kisselev L., Polypeptide release factors in prokaryotes and eukaryotes: same function, different structure. Structure, 2002, vol. 10: 8-9. (Year: 2002).*
Ludke et al., A proteomic study of Corynebacterium glutamicum AAA+ protease FtsH. BMC Microbiol., 2007, 7:6, pp. 1-10 (Year: 2007).*
Shi et al., Economically enhanced succinic acid fermentation from cassava bagasse hydrolysate using Corynebacterium glutamicum immobilized in porous polyurethane filter. Bioresource Technol., 2014, vol. 174: 19-197. (Year: 2014).*
Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

* cited by examiner

*Primary Examiner* — Ganapathirama Raghu
(74) *Attorney, Agent, or Firm* — Rankin, Hill & Clark LLP (57) ABSTRACT

The invention discloses a recombinant *Corynebacterium glutamicum* for producing lysine by biofilm continuous fermentation and a construction method thereof, wherein the recombinant *Corynebacterium glutamicum* is constructed by overexpressing a protease gene FtsH in a *Corynebacterium glutamicum*; and the construction method comprises the following steps of: (1) performing PCR on a genome of the *Corynebacterium glutamicum*, and amplifying the FtsH gene to obtain an amplified FtsH gene segment; (2) cloning the FtsH gene segment on an overexpression plasmid to obtain a recombinant plasmid; and (3) introducing the recombinant plasmid into the *Corynebacterium glutamicum*, and screening to obtain the recombinant *Corynebacterium glutamicum*. The invention has the beneficial effects that the *Corynebacterium glutamicum* for overexpressing the protease FtsH is constructed in the invention, and a film-forming ability of the *Corynebacterium glutamicum* is enhanced, such that a yield of continuous immobilized fermentation of the *Corynebacterium glutamicum* is increased by 38.2% than that of free fermentation of an original bacterium, and a fermentation cycle is shortened by 26.4%.

17 Claims, 4 Drawing Sheets

Specification includes a Sequence Listing.

FIG. 1

Original bacterium                    Recombinant bacterium

RECOMBINANT CORYNEBACTERIUM GLUTAMICUM FOR PRODUCING LYSINE BY BIOFILM CONTINUOUS FERMENTATION AND CONSTRUCTION METHOD THEREOF

TECHNICAL FIELD

The present invention belongs to the field of microorganism and fermentation engineering technologies, and more particularly, relates to a recombinant *Corynebacterium glutamicum* for producing lysine by biofilm continuous fermentation and a construction method thereof.

BACKGROUND

As an amino acid of an aspartic acid family, L-lysine is one of the essential amino acids for human beings and animals that cannot be synthesized by the human beings and the animals, and is widely used in feed additives, food fortifiers and pharmaceutical products, wherein more than 90% lysine products are used as the feed additives.

A biofilm widely exists in nature. In a process of biofilm formation, an extracellular polymeric substance (EPS) secreted by a bacterium itself is a material basis of the biofilm formation, which has a characteristic of layered distribution, and plays a key role in adhesion and aggregation of the bacterium.

A continuous immobilized fermentation technology has been put into production now, wherein the continuous immobilized fermentation performed by the biofilm has achieved initial success. However, there are few reports of continuous immobilized fermentation based on the biofilm in a *Corynebacterium glutamicum*.

As an important industrial strain, the *Corynebacterium glutamicum* has a very weak film-forming ability, and is difficult to realize continuous fermentation. Therefore, we need to perform molecular modification on the *Corynebacterium glutamicum* to enhance a film-forming effect thereof, so as to realize later continuous immobilized fermentation.

It is known that a protease FtsH (EC3.4.24.-) is encoded by an Ngcl 2603 gene in the *Corynebacterium glutamicum*. The FtsH (Filamentation Temperature Sensitive H) belongs to an AAA protease family, and is a membrane-bound protease. The FtsH forms a hexameric ring structure by oligomerization in vivo, and a proteolytic active site is buried in a center of a cavity of a hexameric complex. A keeping module of an FtsH protein comprises an N-terminal transmembrane domain, an AAA structure, a zinc ion binding module, and the like. The FtsH has an ATP enzymatic activity, a proteolytic activity and a molecular chaperone activity, participates in the biofilm formation and protein mass balance control, and is also related to heat shock, hyperosmosis, light stress and other responses.

SUMMARY

Objective of the present invention: a technical problem to be solved by the present invention is to provide a recombinant *Corynebacterium glutamicum* aiming at the defects in the prior art, in order to enhance a film-forming ability of a *Corynebacterium glutamicum* and solve problems that the *Corynebacterium glutamicum* in the prior art has a weak film-forming ability and cannot be used for continuous immobilized fermentation.

A technical problem to be further solved by the present invention is to provide a construction method of the above recombinant *Corynebacterium glutamicum*.

A technical problem to be finally solved by the present invention is to provide an application of the above recombinant *Corynebacterium glutamicum* in producing lysine by biofilm continuous fermentation.

In order to solve the above technical problems, the present invention discloses a recombinant *Corynebacterium glutamicum*, wherein the recombinant *Corynebacterium glutamicum* is constructed by overexpressing a protease gene FtsH in a *Corynebacterium glutamicum*.

A nucleotide sequence of the protease gene FtsH is shown in SEQ ID NO:1.

The *Corynebacterium glutamicum* is ATCC13032.

The overexpressing the protease gene FtsH refers to increasing a copy number of the protease FtsH by introducing a gene sequence of the protease FtsH into an expression vector, thus enhancing an activity of the protease FtsH.

The construction method of the above recombinant *Corynebacterium glutamicum* comprises the following steps of:

(1) performing PCR on a genome of the *Corynebacterium glutamicum* ATCC13032, and amplifying the FtsH gene to obtain a FtsH gene segment with a nucleotide sequence shown in SEQ ID NO:2;

(2) cloning the FtsH gene segment obtained in the step (1) to an overexpression plasmid pXMJ19 to obtain a recombinant plasmid pXMJ19*FtsH; and (3) introducing the recombinant plasmid pXMJ19*FtsH obtained in the step (2) into the *Corynebacterium glutamicum*, and screening to obtain the recombinant *Corynebacterium glutamicum*, wherein:

in the step (1), sequences of primers designed to amplify the FtsH gene are as follows: a nucleotide sequence of a primer 1 is shown in SEQ ID NO:3; and a nucleotide sequence of a primer 2 is shown in SEQ ID NO:4.

In the step (1), the PCR amplification method comprises: denaturating at 94□ for 30 seconds, annealing at 55□ for 30 seconds, extending at 72□ for 2 minutes, and repeating for 30 cycles.

In the step (2), the overexpression plasmid is pXMJ19.

An application of the above *Corynebacterium glutamicum* for overexpressing the protease FtsH in producing lysine is also included in the scope of protection of the present invention, which comprises the following steps of:

(i) inoculating the recombinant *Corynebacterium glutamicum* into a seed medium, and culturing to obtain a seed solution; and (ii) placing a pre-treated immobilization carrier in a fermentation medium, sterilizing the pre-treated immobilization carrier together with the fermentation medium, then inoculating the seed solution into the fermentation medium, and fermenting in batches to obtain a fermentation broth.

After each batch of fermentation, the obtained fermentation broth is replaced with a new fermentation medium for cultivation until sugar is exhausted, and the fermentation is finished to obtain the lysine after about 70 hours; wherein the sugar is a combination of glucose, molasses and sucrose.

In the step (i), concentrations of constituents in the seed medium are: 15 to 35 g/L sucrose, 5 to 15 g/L peptone, 1 to 10 g/L yeast powder, 5 to 10 g/L ammonium sulfate, 0.1 to 1 g/L magnesium sulfate heptahydrate, 1 to 5 g/L potassium dihydrogen phosphate, 5 to 15 g/L dipotassium hydrogen phosphate, and 1 to 5 g/L of urea, and water is used as a solvent; and the cultivation is performed at 28 to 34□ and 200 to 250 rpm for 10 to 14 hours.

In the step (ii), the immobilization carrier is any one or a combination of several of cotton fiber fabric, non-woven fabric, polyester fiber, polyvinyl alcohol fiber, zeolite, bacterial cellulose membrane, silk, bagasse and corn straw; the pre-treatment comprises cutting the immobilization carrier into a square of 2 to 8 cm×2 to 8 cm (preferably 5 cm×5 cm), washing with pure water, drying, soaking in ethanol for 1 hour, then washing with pure water, bathing in boiling water for 10 to 40 minutes (preferably 20 minutes), and drying; a dosage of the immobilization carrier is 1 to 10 g per 500 mL fermentation medium; and the sterilization is performed at 115□ for 15 minutes.

In the step (ii), concentrations of constituents in the fermentation medium are: 80 to 120 g/L glucose, 30 to 50 g/L ammonium sulfate, 0.5 to 1.5 g/L magnesium sulfate, 10 to 25 g/L molasses, 10 to 25 g/L corn steep liquor, 1 to 5 g/L potassium dihydrogen phosphate, 100 to 300 mg/L ferrous sulfate, 100 to 200 mg/L manganese sulfate, 40 to 80 mg/L nicotinamide, 5 to 15 mg/L calcium pantothenate, 5 to 15 mg/L VB1, 0.5 to 2 mg/L copper sulfate, 0.5 to 2 mg/L zinc sulfate, 0.5 to 2 mg/L biotin, and 10 to 50 g/L calcium carbonate, and water is used as a solvent.

In the step (ii), 50 mL of fermentation medium is added into every 500 mL shake flask, and 10% to 30% (v/v) seed solution is inoculated, and fermented at 28 to 34□ and 200 to 250 rpm/min for 60 to 90 hours (preferably 72 hours).

Beneficial effects: compared with the prior art, the present invention has the following advantages.

1. The present invention discloses the method for producing the lysine by the immobilized fermentation of the *Corynebacterium glutamicum*, which uses fibers (cotton fiber fabric, non-woven fabric, polyester fiber, polyvinyl alcohol fiber, bacterial cellulose membrane, silk, bagasse and corn straw) as immobilization materials, and the immobilized bacterium can be reused, and can be continuously fermented.

2. The *Corynebacterium glutamicum* for overexpressing the protease FtsH is constructed in the present invention, and a film-forming ability of the *Corynebacterium glutamicum* is enhanced, such that a yield of continuous immobilized fermentation of the *Corynebacterium glutamicum* is increased by 38.2% than that of free fermentation of an original bacterium, and a fermentation cycle is shortened by 26.4%.

DETAILED DESCRIPTION

The present invention may be better understood from the following embodiments. However, those skilled in the art will easily understand that the contents described in the embodiments are only used to illustrate the present invention, and should not and will not limit the present invention described in detail in the claims.

A plasmid pXMJ19 used in the following embodiments was purchased from Wuhan MIAOLING Biotech Co., Ltd. Unless otherwise specified, all enzymes were purchased from TAKARA, and plasmid extraction and gel recovery kits were purchased from Tiangen.

Embodiment 1: Construct Protease FtsH Overexpression Plasmid

A chromosome of a *Corynebacterium glutamicum* ATCC13032PCR was used for performing PCR, and an FtsH gene was amplified.

Specifically, the PCR was performed by using the following primers 1 and 2 under the following reaction conditions: denaturating at 94□ for 30 seconds, annealing at 55□ for 30 seconds, extending at 72□ for 2 minutes, and repeating for 30 cycles. A gene segment (SEQ ID NO:2) of 2614 bp was amplified.

An amplified sequence contained a coding sequence of FtsH and a 20 bp sequence homologous to a carrier. In addition, the primer 1 had restriction enzyme recognition sites of BamHI, and the primer 2 had restriction enzyme recognition sites of BamHI. The restriction enzyme recognition sites of BamHI were marked in bold.

TABLE 1

| Primer 1 | 5'-gcctgcaggtcgactctagaggatccatgaaaaacaagaaatacct-3' (SEQ ID NO: 3) |
|---|---|
| Primer 2 | 5'-aattcgagctcggtacccgggatccttatccacggttgtctcctt-3' (SEQ ID NO: 4) |

Figure 1:
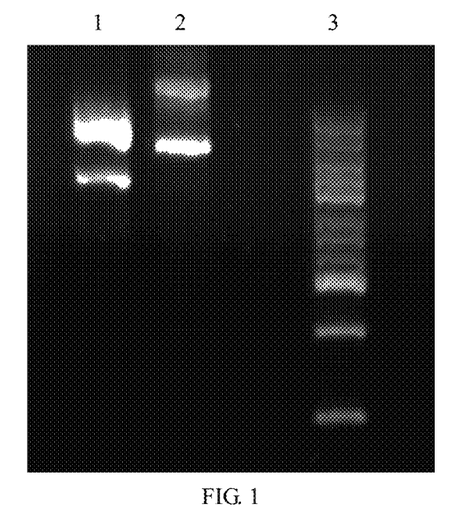
FIG. 1 is an agarose gel electrophoresis of a pXMJ19/*FtsH plasmid. Lane 1 refers to an original plasmid pXMJ19, lane 2 refers to a recombinant plasmid pXMJ19/*FtsH, and lane 3 refers to Marker.

The obtained polynucleotide and the pXMJ19 plasmid treated with the restriction enzyme BamHI were cloned in one step to obtain a recombinant plasmid pXMJ19/*FtsH for overexpressing the protease FtsH gene. An agarose gel electrophoresis was shown in FIG. 1. Lane 1 referred to an original plasmid pXMJ19, lane 2 referred to the constructed plasmid pXMJ19/*FtsH, and lane 3 referred to Marker. A size of the original plasmid pXMJ19 was 6601 bp, while a size of the recombinant plasmid pXMJ19/*FtsH was 9169 bp. It can be seen from the figure that an FtsH gene segment is already inserted into the expression plasmid pXMJ19.

Embodiment 2: Construct Protease FtsH Overexpression Strain

The obtained recombinant plasmid pXMJ19/*FtsH was introduced into a competent cell of a *Corynebacterium glutamicum* ATCC13032, and screened on a LB plate containing 6.5 ug/mL chloramphenicol. After culturing for 2 to 3 days, transformants were picked out, and colony PCR was performed to obtain a recombinant strain of an overexpressed protease FtsH. PCR was performed by using a primer 3 and a primer 4 to verify whether the gene was inserted into the recombinant plasmid.

TABLE 2

| Primer 3 | 5'-ggaattgtgagcggataaca-3' (SEQ ID NO: 5) |
|---|---|
| Primer 4 | 5'-gtatcaggctgaaaatcttc-3' (SEQ ID NO: 6) |

Figure 2:
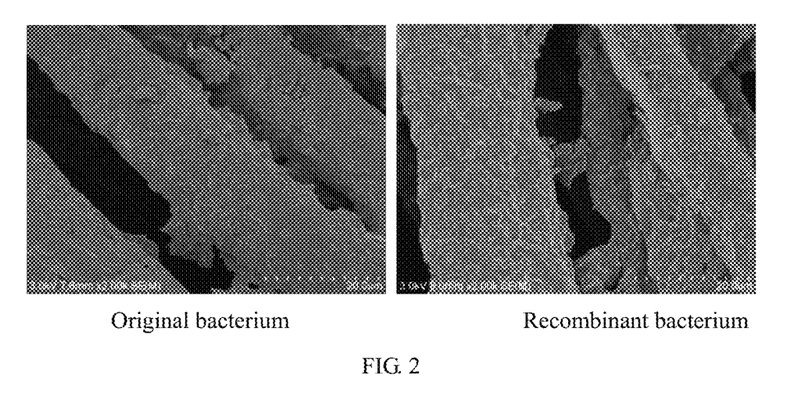
FIG. 2 is an electron micrograph of an original *Corynebacterium glutamicum* ATCC13032 and a recombinant *Corynebacterium glutamicum* ATCC13032.

After successfully constructing a modified strain, 96-well plate and SEM experiments were performed. An electron micrograph was shown in FIG. 2. It can be intuitively and specifically seen from the figure that there are more biofilms of a recombinant bacterium than biofilms of an original bacterium. Continuous immobilized fermentation was performed after enhancing a film-forming effect.

Embodiment 3: Lysine Fermentation Experiment of Recombinant Bacterium (Immobilization of Recombinant Bacterium)

An activation medium was composed of: 10 g/L glucose, 10 g/L peptone, 5 g/L yeast powder and 10 g/L sodium chloride.

A seed medium was composed of: 25 g/L sucrose, 10 g/L peptone, 5 g/L yeast powder, 5 g/L ammonium sulfate, 1 g/L magnesium sulfate heptahydrate, 5 g/L potassium dihydrogen phosphate, 12 g/L dipotassium hydrogen phosphate and 5 g/L urea.

A formula of a fermentation medium comprised: 100 g/L glucose, 40 g/L ammonium sulfate, 1 g/L magnesium sulfate, 20 g/L molasses, 20 g/L corn steep liquor, 1 g/L potassium dihydrogen phosphate, 150 mg/L ferrous sulfate, 100 mg/L manganese sulfate, 50 mg/L nicotinamide, 10 mg/L calcium pantothenate, 10 mg/L VB1, 1 mg/L copper sulfate, 1 mg/L zinc sulfate, 2 mg/L biotin, and 40 g/L calcium carbonate.

5 mL of activation medium was added into every 50 mL centrifuge tube, inoculated with the recombinant bacterium, and activated at 30□ and 220 rpm for 20 hours.

After activation, the mixture was poured into 500 mL shake flask filled with 50 mL seed medium, and cultured at 30□ and 220 rpm for 12 hours.

50 mL of fermentation medium was poured into every 500 mL shake flask, and a carrier was also put into the fermentation medium for sterilization together at 115□ for 15 minutes.

5 mL seed solution was inoculated to the fermentation medium, and fermented at 30□ and 220 rpm for 72 hours.

Figure 5:
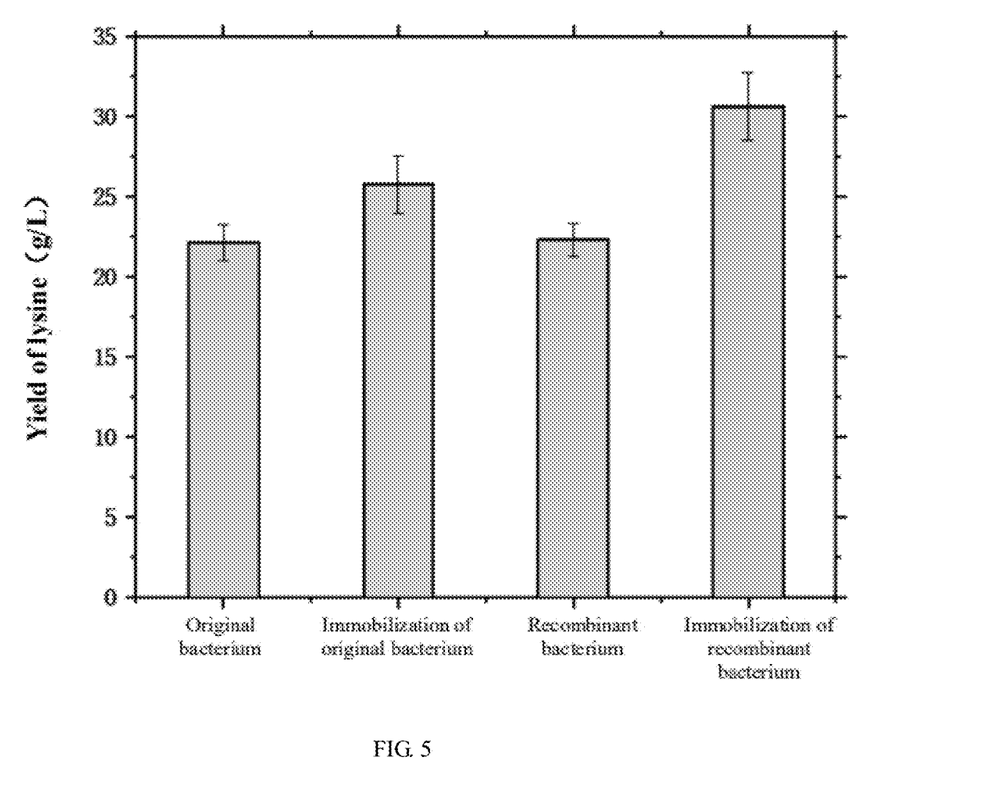
FIG. 5 is a comparison diagram of yields of lysine by immobilized batch fermentation and free fermentation of an original *Corynebacterium glutamicum* ATCC13032 and a recombinant *Corynebacterium glutamicum* ATCC13032.

Continuous immobilized fermentation: during fermentation, the bacterium was already adsorbed on the immobilization carrier in a first batch; at the moment, the shake-flask cultivation had passed for about 72 hours; in a second batch, a fermentation broth was dumped, the immobilization carrier adsorbed with the bacterium was left, and then 50 mL new fermentation medium was poured into the shake flask for cultivation until sugar was exhausted, which lasted for about 60 hours, wherein the sugar was a combination of glucose, molasses and sucrose. Data of a fermentation cycle measured was shown in FIG. 3. A yield of the lysine was shown in FIG. 5. This method was adopted in continuous immobilized fermentation in subsequent batches.

Pre-treatment of cotton fiber carrier material: a cotton fiber carrier was cut into a square of 5 cm×5 cm, washed with pure water, dried, soaked in ethanol for 1 hour, then washed twice with pure water, bathed with boiling water for 20 minutes, put into an oven for drying, weighed to be 1.5 g, and then put into a shake flask filled with the fermentation broth for sterilization together at 115□ for 15 minutes.

Comparative Example 1: Immobilization of Original Bacterium

The recombinant bacterium inoculated in Embodiment 3 was replaced with an original bacterium (the *Corynebacterium glutamicum* ATCC13032), and other steps were the same as those in Embodiment 3. Data of a fermentation cycle measured was shown in FIG. 3. A yield of the lysine was shown in FIG. 5.

Comparative Example 2: Free Fermentation (Recombinant Bacterium) of Recombinant Bacterium No carrier was added into a fermentation medium, and other steps were the same as those in Embodiment 3. Data of a fermentation cycle measured was shown in FIG. 3. A yield of the lysine was shown in FIG. 5.

Comparative Example 3: Free Fermentation (Original Bacteria) of Original Bacterium The recombinant bacterium inoculated in Embodiment 3 was replaced with an original bacterium (the *Corynebacterium glutamicum* ATCC13032), no carrier was added into a fermentation medium, and other steps were the same as those in Embodiment 3. Data of a fermentation cycle measured was shown in FIG. 3. A yield of the lysine was shown in FIG. 5.

Figure 3:
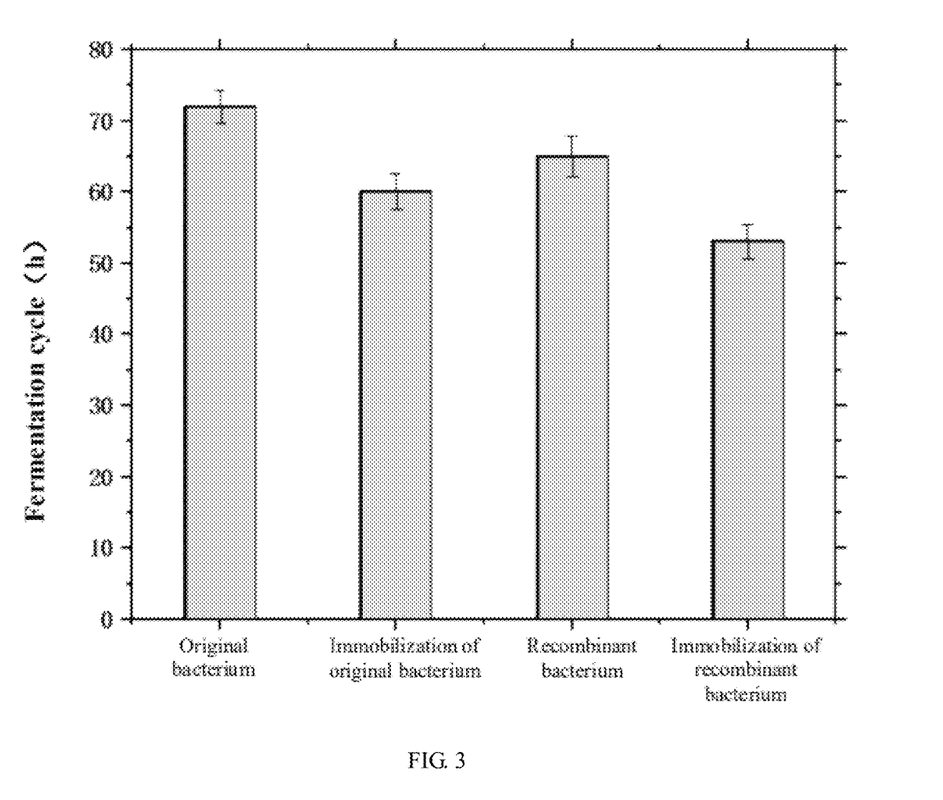
FIG. 3 is a cycle diagram of fermentation of an original *Corynebacterium glutamicum* ATCC13032 and a recombinant *Corynebacterium glutamicum* ATCC13032.

It can be seen from FIG. 3 that compared with the free fermentation, cycles of the immobilized fermentation are all shortened, wherein an immobilized fermentation cycle of the recombinant bacterium is shortened by 26.4% than that of the original bacterium. It can be seen from FIG. 5 that compared with free fermentation, the yield of the lysine obtained by the immobilized fermentation is enhanced, and the immobilized yield of the recombinant bacterium is 38.2% higher than that of the original bacterium. The shortening of the fermentation cycle and the enhancement of the yield of the lysine above are both due to the use of the immobilized fermentation and the recombinant bacteria to enhance a film-forming ability of the *Corynebacterium glutamicum*.

Embodiment 4: Determination Method of Reducing Sugar

DNS (dinitrosalicylic acid) was used to carry out a redox reaction with reducing sugar in an alkaline condition to produce 3-amino-5-nitrosalicylic acid. The product was brown-red when boiled, and a color of the product was proportional to a content of the reducing sugar in a certain concentration range. The content of the reducing sugar was determined by an ultraviolet spectrophotometer (OD540).

A sample was properly diluted to an estimated sugar content ranging from 0.1 mg/mL to 1.0 mg/mL. 0.5 mL diluted sample was added into a 10 mL graduated test tube, and then 0.5 mL DNS was added. The mixture was boiled in boiling water for 5 minutes, and then immediately cooled for 5 minutes. 8 mL pure water was added in the mixture to blend. Moreover, 0.5 mL pure water and 0.5 mL DNS sample were set as blank samples. A standard content curve of the DNS reducing sugar used in this experiment was prepared in advance, and an absorption value was detected by an ultraviolet spectrophotometer at a wave length of 540 nm and used as a magnitude of the content of the reducing sugar.

Embodiment 5: Determination of Content of Lysine

100 μL fermentation broth was sampled from each flask and diluted 50 times with 0.1 M hydrochloric acid solution, then 400 μL of diluent was taken from each sample, followed by PITC pre-column derivatization. A content of the lysine was detected by a RP-HPLC method, and a concentration of the lysine in each sample was calculated.

Continuous immobilized fermentation experiments were performed with an original bacterium and a recombinant bacterium constructed by the present invention. 10 batches of fermentation experiments were performed, and fermentation results were shown in Table 3. It can be seen from FIG. 5 that the yield of the lysine of the modified bacterium subjected to the continuous immobilized fermentation is 38.2% higher than that of the original bacterium subjected to the free fermentation. It can be seen from FIG. 3 that the immobilized fermentation cycle of the modified bacterium is shortened by 26.4% than that of the original bacterium.

TABLE 3

Yield of lysine (g/L) of immobilized bacterium subjected to continuous fermentation in 10 batches

| Batch | First | Second | Third | Fourth | Fifth | Sixth | Seventh | Eighth | Ninth | Tenth |
|---|---|---|---|---|---|---|---|---|---|---|
| Immobilization of original bacterium | 25.79 | 25.18 | 25.73 | 26.12 | 25.47 | 25.91 | 26.55 | 26.01 | 27.51 | 26.37 |
| Immobilization of recombinant bacterium | 30.61 | 29.73 | 30.92 | 32.23 | 31.33 | 31.07 | 32.41 | 31.34 | 32.82 | 32.08 |

Figure 4:
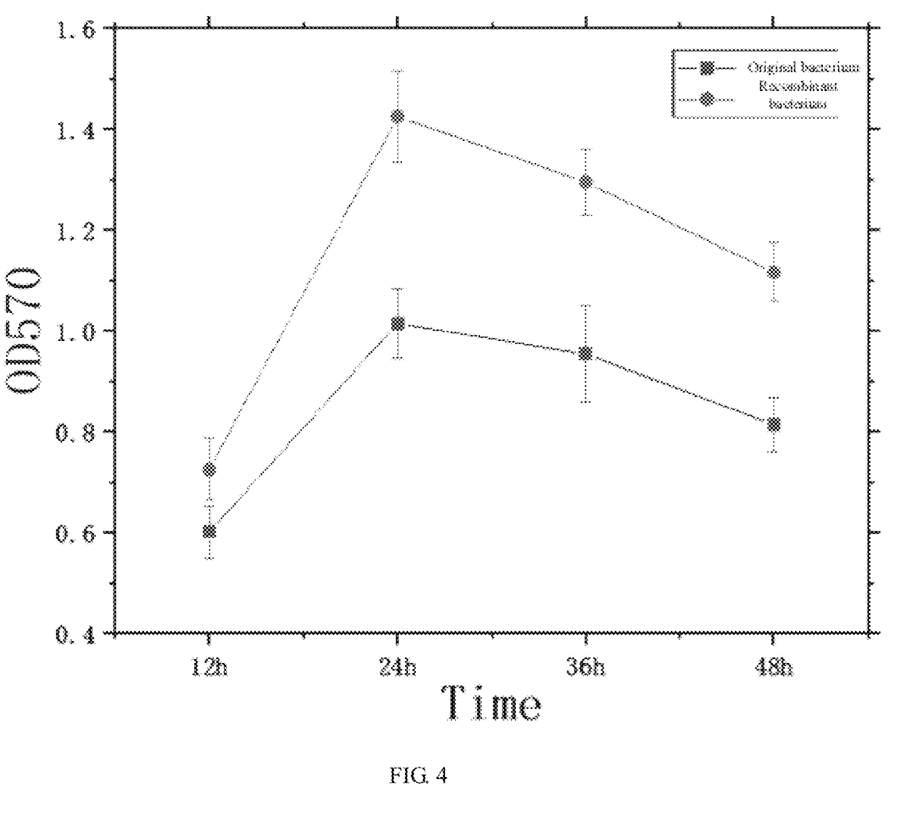
FIG. 4 is experimental data of semi-quantitative measurement of biofilm quantity of an original *Corynebacterium glutamicum* ATCC13032 and a recombinant *Corynebacterium glutamicum* ATCC13032 by crystal violet staining.

Embodiment 6: Semi-Quantitative Measurement of Biofilm Quantity by Crystal Violet Staining 200 uL fermentation medium (without immobilization carrier and calcium carbonate) was added into a colorless 96-well plate, and then 20 uL original bacterium and recombinant bacterium were added respectively. After culturing for 12 hours, 24 hours, 36 hours and 48 hours, and then, OD values at 570 nm were measured by crystal violet staining and a microplate reader. It can be seen from FIG. 4 that a film-forming ability of the recombinant bacterium overexpressing a protease FtsH is obviously enhanced.

The present invention provides the *Corynebacterium glutamicum* overexpressing the protease FtsH, the construction method thereof, as well as the application ideas and methods in producing the lysine. There are many methods and ways to realize the technical solutions. The above is only the preferred embodiments of the present invention. It should be pointed out that those of ordinary skills in the art can make some enhancements and embellishments without departing from the principle of the present invention, and these enhancements and embellishments should also be regarded as falling with the scope of protection of the present invention. All the unspecified components in the embodiments can be realized by the prior art.

REFERENCES TO THE SEQUENCE LISTING

Applicant hereby makes reference to the sequence listing that is submitted in electronic format. The Sequence Listing is provided as a file entitled 49375_SEQLIST.txt, created on Feb. 4, 2021 which is 8,065 bytes in size. The information in the electronic format of the sequence listing is incorporated herein by reference in its entirety.

The invention claimed is:

1. A recombinant *Corynebacterium glutamicum*, comprising the full-length intact polynucleotide sequence of SEQ ID NO:2, wherein the recombinant *Corynebacterium glutamicum* is constructed by overexpressing a protease gene FtsH in a *Corynebacterium glutamicum*.

2. The recombinant *Corynebacterium glutamicum* according to claim 1, wherein the polynucleotide a nucleotide sequence of the protease gene FtsH is SEQ ID NO:1.

3. The recombinant *Corynebacterium glutamicum* according to claim 1, wherein the *Corynebacterium glutamicum* is ATCC13032.

4. A construction method of the recombinant *Corynebacterium glutamicum* according to claim 1, comprising the following steps of:
   (1) performing PCR on a genome of the *Corynebacterium glutamicum* ATCC13032, and amplifying the FtsH gene to obtain an amplified FtsH gene segment with the full-length intact polynucleotide sequence of SEQ ID NO:2;
   (2) cloning the FtsH gene segment obtained in the step (1) to an overexpression plasmid to obtain a recombinant plasmid; and
   (3) introducing the recombinant plasmid obtained in the step (2) into the *Corynebacterium glutamicum*, and screening to obtain the recombinant *Corynebacterium glutamicum*, wherein:
   in the step (1), sequences of primers designed to amplify the FtsH gene are as follows: the oligonucleotide sequence of a primer 1 of SEQ ID NO:3; and the oligonucleotide sequence of a primer 2 of SEQ ID NO:4.

5. The construction method according to claim 4, wherein in the step (1), the PCR amplification method comprises: denaturating at 94° C. for 30 seconds, annealing at 55° C. for 30 seconds, extending at 72° C. for 2 minutes, and repeating for 30 cycles.

6. The construction method according to claim 4, wherein in the step (2), the overexpression plasmid is pXMJ19.

7. A method of using the recombinant *Corynebacterium glutamicum* according to claim 1, comprising producing lysine by fermenting the recombinant *Corynebacterium glutamicum*.

8. The method according to claim 7, comprising the following steps of:
   (i) inoculating the recombinant *Corynebacterium glutamicum* into a seed medium, and culturing to obtain a seed solution; and
   (ii) placing a pre-treated immobilization carrier in a fermentation medium, sterilizing the pre-treated immobilization carrier together with the fermentation medium, then inoculating the seed solution into the fermentation medium, and fermenting in batches to obtain a fermentation broth;
   wherein, after each batch of fermentation, the obtained fermentation broth is replaced with a new fermentation medium for cultivation until sugar is exhausted, and the fermentation is finished to obtain the lysine.

9. The method according to claim 8, wherein in the step (i), concentrations of constituents in the seed medium are: 15 to 35 g/L sucrose, 5 to 15 g/L peptone, 1 to 10 g/L yeast powder, 5 to 10 g/L ammonium sulfate, 0.1 to 1 g/L magnesium sulfate heptahydrate, 1 to 5 g/L potassium dihydrogen phosphate, 5 to 15 g/L dipotassium hydrogen phosphate, and 1 to 5 g/L urea, and water is used as a solvent; and the cultivation is performed at 28 to 34° C. and 200 to 250 rpm for 10 to 14 hours.

10. The method according to claim 8, wherein in the step (ii), the immobilization carrier is any one or a combination of several of cotton fiber fabric, non-woven fabric, polyester fiber, polyvinyl alcohol fiber, zeolite, bacterial cellulose membrane, silk, bagasse and corn straw; the pre-treatment comprises cutting the immobilization carrier into a square of 2 to 8 cm×2 to 8 cm, washing with pure water, drying, soaking in ethanol, then washing with pure water, bathing in boiling water for 10 to 40 minutes, and drying; and a dosage of the immobilization carrier is 1 to 10 g per 500 mL fermentation medium.

11. The method according to claim 8, wherein in the step (ii), concentrations of constituents in the fermentation medium are: 80 to 120 g/L glucose, 30 to 50 g/L ammonium sulfate, 0.5 to 1.5 g/L magnesium sulfate, 10 to 25 g/L molasses, 10 to 25 g/L corn steep liquor, 1 to 5 g/L potassium dihydrogen phosphate, 100 to 300 mg/L ferrous sulfate, 100 to 200 mg/L manganese sulfate, 40 to 80 mg/L nicotinamide, 5 to 15 mg/L calcium pantothenate, 5 to 15 mg/L VB1, 0.5 to 2 mg/L copper sulfate, 0.5 to 2 mg/L zinc sulfate, 0.5 to 2 mg/L biotin, and 10 to 50 g/L calcium carbonate, and water is used as a solvent; and the fermentation is performed at 28 to 34° C. and 200 to 250 rpm for 60 to 90 hours.

12. A construction method of the recombinant *Corynebacterium glutamicum* according to claim 2, comprising the following steps of:
(1) performing PCR on a genome of the *Corynebacterium glutamicum* ATCC13032, and amplifying the FtsH gene to obtain an amplified FtsH gene segment with the full-length intact polynucleotide sequence of SEQ ID NO:2;
(2) cloning the FtsH gene segment obtained in the step (1) to an overexpression plasmid to obtain a recombinant plasmid; and
(3) introducing the recombinant plasmid obtained in the step (2) into the *Corynebacterium glutamicum*, and screening to obtain the recombinant *Corynebacterium glutamicum*, wherein:
in the step (1), sequences of primers designed to amplify the FtsH gene are as follows: the oligonucleotide sequence of a primer 1 of SEQ ID NO:3; and the oligonucleotide sequence of a primer 2 of SEQ ID NO:4.

13. The construction method according to claim 12, wherein in the step (1), the PCR amplification method comprises: denaturating at 94° C. for 30 seconds, annealing at 55° C. for 30 seconds, extending at 72° C. for 2 minutes, and repeating for 30 cycles.

14. The construction method according to claim 12, wherein in the step (2), the overexpression plasmid is pXMJ19.

15. A construction method of the recombinant *Corynebacterium glutamicum* according to claim 3, comprising the following steps of:
(1) performing PCR on a genome of the *Corynebacterium glutamicum* ATCC13032, and amplifying the FtsH gene to obtain an amplified FtsH gene segment with the full-length intact polynucleotide sequence of SEQ ID NO:2;
(2) cloning the FtsH gene segment obtained in the step (1) to an overexpression plasmid to obtain a recombinant plasmid; and
(3) introducing the recombinant plasmid obtained in the step (2) into the *Corynebacterium glutamicum*, and screening to obtain the recombinant *Corynebacterium glutamicum*, wherein:
in the step (1), sequences of primers designed to amplify the FtsH gene are as follows: the oligonucleotide sequence of a primer 1 of SEQ ID NO:3; and the oligonucleotide sequence of a primer 2 of SEQ ID NO:4.

16. The construction method according to claim 15, wherein in the step (1), the PCR amplification method comprises: denaturating at 94° C. for 30 seconds, annealing at 55° C. for 30 seconds, extending at 72° C. for 2 minutes, and repeating for 30 cycles.

17. The construction method according to claim 15, wherein in the step (2), the overexpression plasmid is pXMJ19.

* * * * *

SEQUENCE LISTING

```
<160> NUMBER OF SEQ ID NOS: 6

<210> SEQ ID NO 1
<211> LENGTH: 2562
<212> TYPE: DNA
<213> ORGANISM: Corynebacterium glutamicum

<400> SEQUENCE: 1
atgaaaaaca agaaatacct gcagttcggc ggtatcgcag ccgtaatcct catcgttctg      60
ttcttggtgt ccctgtttag cagtgacacc aggaacttcc aggaggtcga tacctctgtt     120
gcgatggcac agcttgacgc cggaaacgtc gccgaagctc aaatcgatga cagggaacag     180
cgcgtccgac tgaccttgcg tgaacccatc acggtggatg aacgcgaagg cgttgaagag     240
atcctcgcgc agtacccagc tcgtaccgcg ccagcgatct tgagaaggt ggaagcatcc      300 aacactgatt cctataccac caatgtgacg caggagagct tcctgatgtc catgctgagc     360
ttcatcctgc cgatggtgat catcttcggt ttgctgatgt tcttcctcac ccgcatgcag     420
ggtggtggca tgtttggcat cggtggatcc aaggccaagc agctgaccaa ggatatgccc     480
accaacacct tcgcggatgt tgctggcgct gaagaagcag tggatgaact ccatgagatc     540
aaggacttcc tggaagaccc cacccgctac gaagccctcg gagcgaaaat ccctcgtggt     600
gtgctgcttt acggccctcc cggtactggt aaaaccctgc tggctcgtgc cgtagctggt     660
gaggctggcg tgccgttcta ctcaatttcc ggttctgact ttgtggaaat gttcgtcggt     720
gttggtgcct cgcgtgtgcg tgatctgttt aagcaggcca aggaaaacag tccctgcatc     780
atcttcgtcg atgagatcga tgcggttggt cgcgcccgtg gctcaggaat gggtggcgga     840
cacgatgagc gtgaacagac cctgaaccag ttgctcgttg agatggatgg ctttggtgat     900
cgtcaaggcg tcattctgat ggctgctacc aaccgcccag atgttcttga cccagcgctg     960
```

```
ctgcgtcctg gccgtttcga ccgccagatc ccagtcacca accctgacct acgcggccgt    1020
gaacagatcc tggaagttca cgccaagggt aagccttttcg cacccgatgc agatatcaag    1080
gcattggcaa agcgcaccgc cggcatgtcc ggcgctgacc tggcaaacgt gcttaacgaa    1140
gccgcgctgc taaccgcccg cgtgggtggc aacgtgatca ccgccgacgc tctggaagaa    1200
gcaaccgacc gcgttgtcgg tggaccacgt cgctccggca aggtgatttc cgagaaggaa    1260
aagaaggtca ccgcctacca cgaaggtgga cacaccctgt ccgcatgggc gttggaagac    1320
atcgagcgcg tctacaaggt caccatcttg gcccgcggtc gcaccggcgg tcacgccatg    1380
actgcccaag aagatgacaa gggcatgtac aaccgcaacg aattgttcgc cgcctggtc    1440 tttgccatgg gtggacgctc cgcggaagaa ctagtcttcg gcgaacccac caccggcgcc    1500
tccgccgata ttgaaatggc caccaagatc gcccgatcca tggtgaccga atatggcatg    1560
tccccagctg tcggcatggt gaaatacggc caagaacagg gcgacccatt ctccggacgc    1620
ggtggcggtg aaacttgga ccactcccaa gaagtcgcag caaccatcga caccgaagtc    1680
cagttcctcc tggacaaagc ccatgaagtg tcctactcca cctggctga ataccgcgac    1740 cacctggacc gcctcgcgga aaaactcctg gaaaaggaaa ccctgcgacg cccagacctc    1800
gaagcgcttt tcgacgacat cgtcccacgc aaggtcgccg aagtcttccc cgacgagtcc    1860
acacgattcc ctcgccaaga aaaccgcgaa ccagtaaaaa ccccagtgga gctcgcactg    1920
gaacgtggcg aagaaccacc aaagaagttc tccattcttg aggcctcccg cgcaacccgc    1980
gaacgccgtc gcaaggaatt ggaagctcag ggtaagttgc cggtgcagcc tgcgtcttct    2040
gccggcgtgg cacctgcggc cggagcagct gccggatcct atggcacccc acctccagct    2100
gattggagcg tgcccggttc cgctggaaag caccgctcac gtgcagaaga acagccagct    2160
gagcagggct tccggctca gaccccggca caagctcctg agcagtcccc tgattcaagt    2220
ggcggccgcc ccaacccttta cgcgactcca accgcatccg gtgagcaccc tggtatgaag    2280
gcctatggct tcggcgattc cgaactcatg gaccaatcaa caggtgcgga acataccccca    2340 ggtaacgttt cacaggaatc cccaaccgaa atgatcgggt ccgtttgccc ggatcatgaa    2400
cgttcggact acccagaaaa ggcgcaaaaa gagtcggtgc tggatgcttc tgaaaccaca    2460
gaaatgcctg tcgttccaga tcagcccatc gatggtgatt ccgggaagtc cgctgagggc    2520
acacaggaga atccggaaaa tgaaggagac aaccgtggat aa                        2562
```

<210> SEQ ID NO 2
<211> LENGTH: 2614
<212> TYPE: DNA
<213> ORGANISM: Artificial Sequence
<220> FEATURE:
<223> OTHER INFORMATION: Amplified FtsH gene segment

<400> SEQUENCE: 2

```
gcctgcaggt cgactctaga ggatccatga aaaacaagaa ataccctgcag ttcggcggta      60 tcgcagccgt aatcctcatc gttctgttct tggtgtccct gtttagcagt gacaccagga     120
acttccagga ggtcgatacc tctgttgcga tggcacagct tgacgccgga aacgtcgccg     180
aagctcaaat cgatgacagg gaacagcgcg tccgactgac cttgcgtgaa cccatcacgg     240
tggatgaacg cgaaggcgtt gaagagatcc tcgcgcagta cccagctcgt accgcgccag     300
cgatctttga gaaggtggaa gcatccaaca ctgattccta taccaccaat gtgacgcagg     360
agagcttcct gatgtccatg ctgagcttca tcctgccgat ggtgatcatc ttcggtttgc     420
tgatgttctt cctcacccgc atgcagggtg gtggcatgtt tggcatcggt ggatccaagg    480
```

```
ccaagcagct gaccaaggat atgcccacca acaccttcgc ggatgttgct ggcgctgaag      540
aagcagtgga tgaactccat gagatcaagg acttcctgga agaccccacc cgctacgaag      600
ccctcggagc gaaaatccct cgtggtgtgc tgctttacgg ccctcccggt actggtaaaa      660
ccctgctggc tcgtgccgta gctggtgagg ctggcgtgcc gttctactca atttccggtt      720
ctgactttgt ggaaatgttc gtcggtgttg gtgcctcgcg tgtgcgtgat ctgtttaagc      780
aggccaagga aaacagtccc tgcatcatct tcgtcgatga gatcgatgcg gttggtcgcg      840
cccgtggctc aggaatgggt ggcggacacg atgagcgtga acagaccctg aaccagttgc      900
tcgttgagat ggatggcttt ggtgatcgtc aaggcgtcat tctgatggct gctaccaacc      960
gcccagatgt tcttgaccca cgctgctgc gtcctggccg tttcgaccgc cagatcccag     1020
tcaccaaccc tgacctacgc ggccgtgaac agatcctgga agttcacgcc aagggtaagc     1080
ctttcgcacc cgatgcagat atcaaggcat ggcaaagcg caccgccggc atgtccggcg     1140
ctgacctggc aaacgtgctt aacgaagccg cgctgctaac cgcccgcgtg ggtggcaacg     1200
tgatcaccgc cgacgctctg gaagaagcaa ccgaccgcgt tgtcggtgga ccacgtcgct     1260
ccggcaaggt gatttccgag aaggaaaaga aggtcaccgc ctaccacgaa ggtgacaca     1320 ccctgtccgc atgggcgttg aagacatcg agcgcgtcta caaggtcacc atcttggccc     1380
gcggtcgcac cggcggtcac gccatgactg cccaagaaga tgacaagggc atgtacaacc     1440
gcaacgaatt gttcgcccgc ctggtctttg ccatgggtgg acgctccgcg gaagaactag     1500
tcttcggcga acccaccacc ggcgcctccg ccgatattga aatggccacc aagatcgccc     1560
gatccatggt gaccgaatat ggcatgtccc cagctgtcgg catggtgaaa tacggccaag     1620
aacagggcga cccattctcc ggacgcgtg gcggtggaaa cttggaccac tcccaagaag     1680
tcgcagcaac catcgacacc gaagtccagt tcctcctgga caaagcccat gaagtgtcct     1740
actccatcct ggctgaatac cgcgaccacc tggaccgcct cgcggaaaaa ctcctggaaa     1800
aggaaaccct gcgacgccca gacctcgaag cgcttttcga cgacatcgtc ccacgcaagg     1860
tcgccgaagt cttccccgac gagtccacac gattccctcg ccaagaaaac cgcgaaccag     1920
taaaaacccc agtggagctc gcactggaac gtggcgaaga accaccaaag aagttctcca     1980
ttcttgaggc ctcccgcgca acccgcgaac gccgtcgcaa ggaattggaa gctcagggta     2040
agttgccggt gcagctgcg tcttctgccg gcgtggcacc tgcggccgga gcagctgccg     2100
gatcctatgg cacccacct ccagctgatt ggagcgtgcc cggttccgct ggaaagcacc     2160
gctcacgtgc agaagaacag ccagctgagc agggcttccc ggctcagacc ccggcacaag     2220
ctcctgagca gtcccctgat tcaagtggcg gccgccccaa cccttacgcg actccaaccg     2280
catccggtga gcaccctggt atgaaggcct atggcttcgg cgattccgaa ctcatggacc     2340
aatcaacagg tgcggaacat accccaggta acgtttcaca ggaatcccca accgaaatga     2400
tcgggttccg tttgccggat catgaacgtt cggactaccc agaaaaggcg caaaagagt     2460 cggtgctgga tgcttctgaa accacagaaa tgcctgtcgt tccagatcag cccatcgatg     2520
gtgattccgg gaagtccgct gagggcacac aggagaatcc ggaaaatgaa ggagacaacc     2580
gtggataagg atccccgggt accgagctcg aatt                                2614
```

<210> SEQ ID NO 3
<211> LENGTH: 46
<212> TYPE: DNA
<213> ORGANISM: Artificial Sequence
<220> FEATURE:

```
<223> OTHER INFORMATION: Primer 1 (DNA)

<400> SEQUENCE: 3
gcctgcaggt cgactctaga ggatccatga aaaacaagaa atacct          46

<210> SEQ ID NO 4
<211> LENGTH: 46
<212> TYPE: DNA
<213> ORGANISM: Artificial Sequence
<220> FEATURE:
<223> OTHER INFORMATION: Primer 2 (DNA)

<400> SEQUENCE: 4
aattcgagct cggtacccgg ggatccttat ccacggttgt ctcctt          46

<210> SEQ ID NO 5
<211> LENGTH: 20
<212> TYPE: DNA
<213> ORGANISM: Artificial Sequence
<220> FEATURE:
<223> OTHER INFORMATION: Primer 3 (DNA)

<400> SEQUENCE: 5
ggaattgtga gcggataaca                                       20

<210> SEQ ID NO 6
<211> LENGTH: 20
<212> TYPE: DNA
<213> ORGANISM: Artificial Sequence
<220> FEATURE:
<223> OTHER INFORMATION: Primer 4 (DNA)

<400> SEQUENCE: 6
gtatcaggct gaaaatcttc                                       20
```